United States Patent

Guo et al.

[11] Patent Number: 6,033,866
[45] Date of Patent: *Mar. 7, 2000

[54] HIGHLY SENSITIVE AMPEROMETRIC BI-MEDIATOR-BASED GLUCOSE BIOSENSOR

[75] Inventors: Dingli Guo, Union City; Paul Shieh, Fremont; Esfir Goldberg, San Francisco, all of Calif.

[73] Assignee: Biomedix, Inc., Fremont, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/986,974

[22] Filed: Dec. 8, 1997

[51] Int. Cl.[7] .............................. C12Q 1/54; C12Q 1/00; C12Q 1/26; C12Q 1/28

[52] U.S. Cl. .................................. 435/14; 435/4; 435/25; 435/28; 435/817; 435/289.1; 435/283.1; 205/263; 205/571

[58] Field of Search ..................... 435/14, 4, 25, 435/28, 817, 289.1, 283.1; 205/263, 571

[56] References Cited

U.S. PATENT DOCUMENTS

| | | | |
|---|---|---|---|
| 4,545,382 | 10/1985 | Higgins et al. | 128/635 |
| 4,830,959 | 5/1989 | McNeil et al. | 435/7 |
| 5,108,566 | 4/1992 | Szuminsky et al. | 204/153.12 |
| 5,225,064 | 7/1993 | Henkens et al. | 204/403 |
| 5,264,106 | 11/1993 | McAleer et al. | 204/403 |
| 5,312,590 | 5/1994 | Gunasingham | 422/56 |
| 5,522,977 | 6/1996 | Shieh | 204/403 |
| 5,645,710 | 7/1997 | Shieh | 435/14 |
| 5,695,947 | 12/1997 | Guo et al. | 435/14 |
| 5,779,867 | 7/1998 | Shieh | 204/403 |

OTHER PUBLICATIONS

Zhao et al, "Stable Mediated Amperometric Biosensors Using a Graphite Electrode Embedded With Tetrathiafulvalene In Silicone Oil" *Biosensors & Bioelectrics* vol. 8, pp. 483–491, (1993).

(List continued on next page.)

*Primary Examiner*—Louise N. Leary
*Attorney, Agent, or Firm*—Marvin S. Aronoff

[57] ABSTRACT

A highly sensitive sensor for the amperometric assay of glucose in aqueous media having a face-to-face sandwich configuration is provided which comprises a sensing electrode strip containing a first redox mediator in an electrically conductive coating and a reference electrode strip in simultaneous contact with a reagent strip containing a second redox mediator which is sandwiched between the active electrode surfaces. An opening is provided in the reference electrode for the introduction of samples. In one embodiment, a whole blood separation membrane is interposed between the reference electrode and the reagent strip to filter red blood cells and other particles from whole blood to enable direct assay of glucose without sample preparation. The sensing electrode comprises a non-conductive support member having an electrically conductive layer containing the first redox mediator. The reference electrode is typically a Ag/AgCl electrode formed by coating an ink containing Ag/AgCl dispersed in a resin on a non-conductive base. The reagent strip is a porous or fibrous carrier, typically a paper, impregnated with a mixture containing the second redox mediator, glucose oxidase, horseradish peroxidase, at least one surfactant and at least one stabilizer comprising an aqueous thickening agent. In one version of the sensor, the sensing electrode comprises a support member of polyester film coated with an electrically conductive graphite composition containing dimethylferrocene as the first redox mediator and the second redox mediator comprises potassium ferrocyanide.

22 Claims, 5 Drawing Sheets

OTHER PUBLICATIONS

Matthews et al, *The Lancet*, pp. 778–779, (1987).

Cass et al, *Analytical Chemistry*, vol. 56, pp. 667–661 (1984).

Persson et al, *Biosensors & Bioelectronics*, vol. 8, pp. 81–88 (1993).

Atanasov et al, *Biosensors & Bioelectronics* vol. 7, pp. 361–365 (1992).

Marcinkeviciene et al, *Biosensors & Bioelectronics*, vol. 8, pp. 209–212 (1993).

Zakeerudin et al. "Glucose Oxidase Mediation by Soluble and Immobilized Electroactive Detergents" *Biosensors & Bioelectronics*, vol. 11, pp. 305–316 (1996).

Alegret et al. "Carbon–Polymer Biocomposites For Amperometric Sensing" *Biosensors & Bioelectronics*, vol. 11, No. 1/2, pp. 35–44 (1996).

HIGHLY SENSITIVE AMPEROMETRIC BI-MEDIATOR-BASED GLUCOSE BIOSENSOR

BACKGROUND OF THE INVENTION

Although there are numerous methods for the quantitative determination of glucose in biological fluids, there is a need for a simple, rapid, highly sensitive, accurate and reproducible means which can be easily miniaturized, inexpensively produced, and which is inexpensive to use. Such means would be especially useful, convenient and less painful to the patient when screening for and monitoring diabetes in the human if only a few drops of blood were required for a reliable test. Such a simple to use, rapid and reliable means to assay glucose could be used to monitor blood glucose levels at the hospital bedside, in a physician's office and as a home diagnostic tool to monitor the glycemic state of diabetics. The usefulness of such means would be enhanced if it had sufficiently sensitivity and accuracy to be applied to the quantitative determination of glucose concentrations in urine, which generally are far lower than in the blood. In addition, a simple, rapid, economical and convenient means which can be applied to the on-site monitoring of glucose concentrations during food processing and in agricultural products is needed. Furthermore, there is a need to increase the convenience and rapidity of glucose assays and to reduce the possibility of inaccurate results due to operator error in the preparation and use of aqueous solutions, by eliminating the need to prepare or mix such solutions prior to performing the assay.

Amperometric assay is an approach to the rapid assay of glucose in human or animal blood and other biological fluids which has been tried with varying degrees of success. Such assays utilize sensing electrodes in conjunction with a single redox mediator and a combination of oxidative and hydrolytic enzymes.

For example, Zhao et al (*Biosensors & Bioelectronics* vol. 8, pp 483–491, 1993) use tetrathiafulvalene (TTF) as a mediator dissolved in silicone oil and embedded in a graphite disc electrode in combination with immobilized glucose oxidase. Matthews et al (*The Lancet*, pp. 778–779, 1987) describe a pen sized digital blood glucose meter that uses ferrocene as a mediator, and a single use disposable strip on which dry glucose oxidase is deposited. Earlier work by Cass et al (*Analytical Chemistry*, vol. 56, pp 667–661 (1984) demonstrated the use of a ferrocene mediated enzyme electrode for the amperometric determination of glucose. Persson et al (*Biosensors & Bioelectronics*, vol. 8, pp 81–88 1993) described amperometric biosensors based on redox polymer-mediated electron transfer from NADH to carbon paste electrodes. Atanasov et al (*Biosensors & Bioelectronics* vol. 7, pp 361–365 (1992) demonstrated amperometric glucose biosensors using a porous carbon black matrix in which either 1,1'-dimethylferrocene or nickelocene or tetracyanoquinodimethane served as mediators. Marcinkeviciene et al (*Biosensors & Bioelectronics*, vol. 8, pp 209–212 (1993) used a ferrocyanide mediator in a strip type glucose biosensor.

Although amperometric sensors using a single mediator can be used to assay glucose, none really provides the combination of a wide response range, rapid response, a high degree of accuracy and precision over a wide response range and high sensitivity so that even relatively low concentrations of glucose such as found in urine could be assayed. In addition, there is no glucose biosensor which combines these attributes in a manner that allows easy and convenient use by untrained consumers.

BRIEF DESCRIPTION OF THE INVENTION

The present invention is directed to meeting the foregoing needs by providing an amperometric glucose biosensor that is based on a two mediator-two enzyme redox system. The term redox mediator or mediator is herein defined as a substance or substances that facilitates the flow of electrons in a reduction-oxidation reaction, so that the reaction may occur at a lower potential than when such substance of substances are absent. The sensitivity of said amperometric glucose biosensor is markedly enhanced in one embodiment in which the electrodes are arranged in a face-to-face sandwich with the first redox mediator contained in the conductive layer of the sensing electrode and the second redox mediator contained in the reagent strip sandwiched between these electrodes. In addition to high sensitivity, said amperometric glucose biosensor exhibits a wide range of linearity thus enabling the direct and rapid measurement of glucose in biological fluids such as serum, plasma, whole blood or urine and in foodstuffs and agricultural produce and other aqueous media without sample dilution or concentration. It is especially useful for the rapid assay of glucose levels in whole blood without sample dilution. The glucose biosensor generally comprises a sensing electrode having a redox mediator dispersed in an electrically conductive medium such as an electrically conductive graphite formulation; a reference electrode such as a standard silver-silver chloride (Ag/AgCl) or calomel electrode; and a reagent strip containing reagents, enzymes and a second redox mediator system, with the reagent strip in simultaneous contact with the sensing electrode and the reference electrode. The reagent strip contains a second redox mediator system, glucose oxidase and horseradish peroxidase in a stabilizing gel medium. The electrically conductive medium of the sensing electrode contains a first redox mediator such as dimethylferrocene (DMF), ferricinium, ferrocene monocarboxylic acid (FCOOH), 7,7,8,8-tetracyanoquinodimethane (TCNQ), tetrathiafulvalene (TTF), nickelocene (Nc), N-methylacridinium (NMA$^+$), tetrathiatetracene (TTT), N-methylphenazinium (NMP$^+$), hydroquinone or mixtures thereof. The second redox mediator contained in the reagent strip may comprise a) various oxidizable compounds and mixtures such as 3-methyl-2-benzothiazolinone hydrazone hydrochloride and 3-dimethylaminobenzoic acid (MBTH-DMAB), 3-methyl-2-benzothiozolinone hydrazone and 2-methoxy-4-allyl phenol, 4-aminoantipyrine (AAP) and dimethylaniline, 4-aminoantipyrene and 4-methoxynaphthol, 3,3',5,5'-tetramethylbenzidine (TMB), 2,2-azino-di-[3-ethyl-benzthiazoline sulfonate], o-dianisidine, o-toluidine, sulfonated 2,4-dichloro-phenol and 4-amino phenazone, benzidine, or b) various redox compounds, ions and complexes such as CN$^-$, Fe(CN)$_6^{-4}$, I$^-$, Co(NH$_3$)$_6^{++}$, Sn$^{++}$, S$^{-2}$ or Tl$^{+2}$.

In one embodiment the biosensor also includes a membrane on top of the reagent strip to retain red blood cells and other formed bodies thus allowing only plasma or serum to pass through to the reagent strip thereby eliminating interference with the precision and reproducibilty of the assay produced by such formed bodies.

The sensor may be constructed in several physical forms. For example, both the electrode and the reference electrode may be formed as coatings on separate non-conductive strips such as polyester film strips with these strips arranged so that they form a sandwich with the reagent strip sandwiched between the two electrode strips and in simultaneous contact with the active, electrically conductive, surfaces of the electrode strips. When the sensor is constructed in the sandwich configuration an opening is created in one or both of the electrode strips so that the reagent strip is exposed, enabling test samples to be placed on the reagent strip. An opening in the reference electrode is preferred. In any version of the sensor having a whole blood separation membrane, this membrane is situated between any opening for the introduction of test samples and the reagent strip so that a test sample must pass through the whole blood separation membrane before contacting the reagent strip.

In another form, the separate strips on which the sensing and reference electrodes were formed are arranged side-by-side with a small separation between the strips, and the membrane reagent strip placed so that it forms a bridge between the two electrodes and is in simultaneous contact with the active, electrically conductive, surfaces of the sensing and reference electrodes.

In yet another form, both the sensing electrode and the reference electrode are formed on a common non-conductive support with a gap separating them. The reagent strip is then placed so that it forms a bridge between the two electrodes and is in simultaneous contact with the active, electrically conductive, surfaces of the sensing and reference electrodes. In this configuration a non-conductive protective cover such as a non-conductive film having an opening through which sample may be introduced may be placed over the reagent strip.

DESCRIPTION OF THE PREFERRED EMBODIMENTS

Figure 1A:
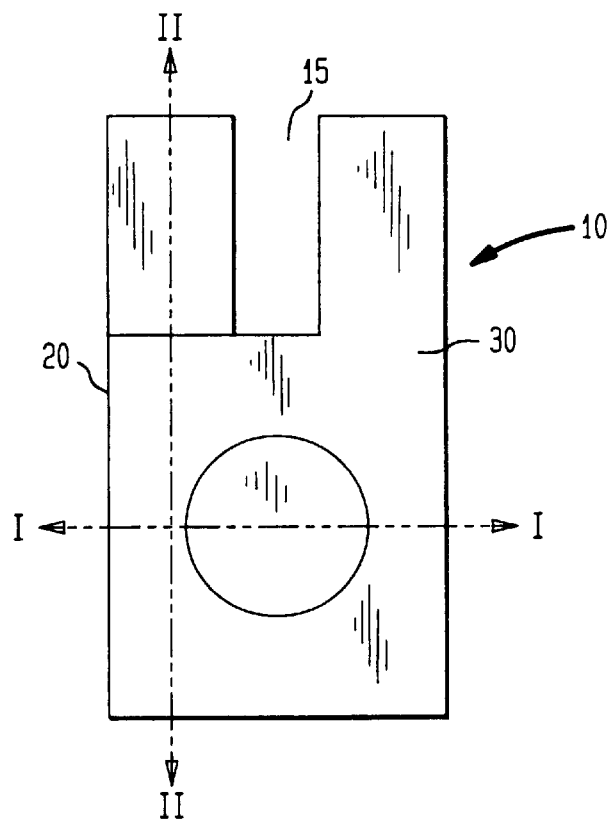
FIG. 1A is a top view of a version of the glucose sensor of the present invention having a sandwich configuration.
Figure 1B:
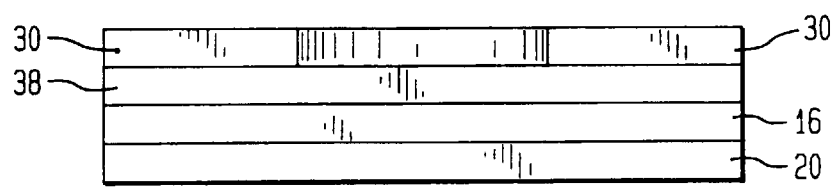
FIG. 1B is a cross-sectional view along line I—I of the glucose sensor of FIG. 1A.
Figure 1C:
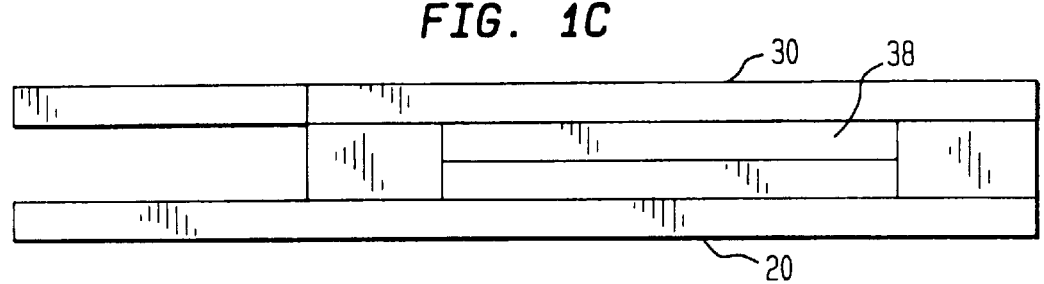
FIG. 1C is a cross-sectional view along line II—II of the glucose sensor of FIG. 1A.
Figure 1D:
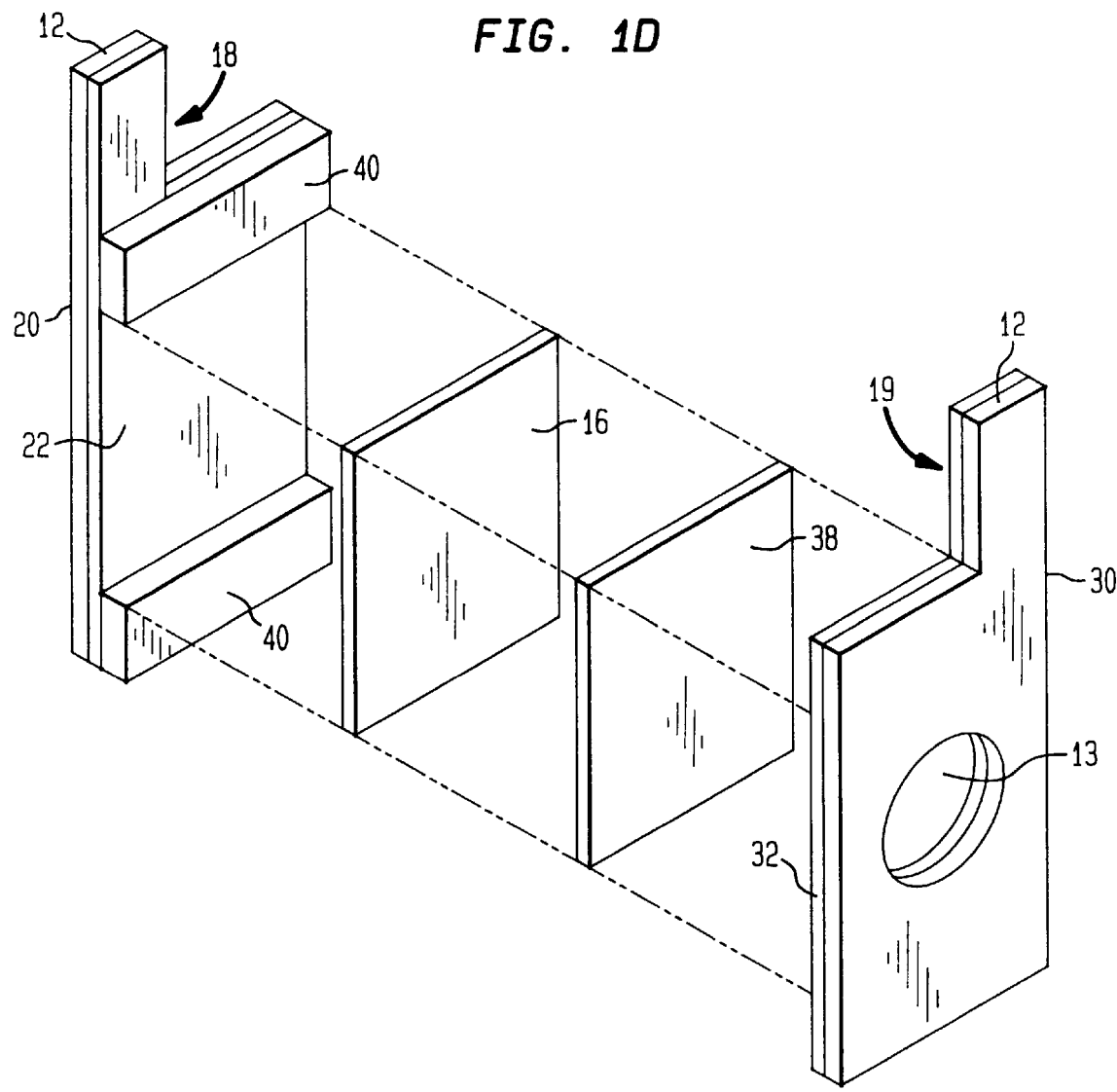
FIG. 1D is an exploded view of the glucose sensor of FIG. 1A.
Figure 2:
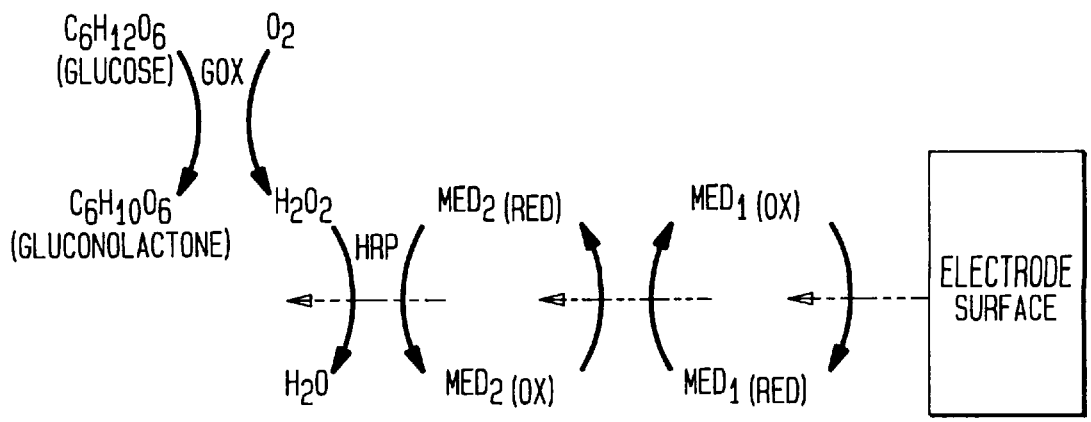
FIG. 2 is a redox process scheme for electron flow in the glucose sensor having redox mediators in the sensing electrode and in the reagent strip.

The following abbreviations used in the description of different embodiments of the invention are hereby defined:

DMF—1,1'dimethylferrocene
TCNQ—7,7,8,8-tetracyanoquinodimethane
TTF—tetrathiafulvalene
Nc—nickelocene
FCOOH—ferrocene monocarboxylic acid
NMP—phenazine methysulphate
TMB—3,3',5,5'tetramethylbenzidine
MBTH-DMAB—3-methyl-2-benzothiazolinone hydrazone hydrochloride and 3-dimethylaminobenzoic acid MEGA-3—octanoyl-N-methyl-D-glucamide
MEGA-10—decanoyl-N-methyl-D-glucamide
Surfynol 485—2,4,7,9-tetramethyl-5-decyne-4,7-diol ethoxylate(30) (Air Products & Cemicals Inc.)
AAP—4-aminoantipyrene
PVC—polyvinyl chloride
GOX—glucose oxidase
HRP—horseradish peroxidase
$MED_1$—first mediator
$MED_2$—second mediator FIG. 1A is a top view of an embodiment of the amperometric glucose biosensor 10 of the present invention having a face-to-face sandwich configuration. FIG. 1B is a cross-sectional view along line I—I of FIG. 1A, FIG. 1C is a cross-sectional view along line II—II of FIG. 1A. FIG. 1D is an exploded view of the face-to-face sandwich configuration of FIG. 1A. A whole blood separation membrane 38 is shown in place in this embodiment. The whole blood separation membrane filters formed elements such as red blood cells from whole blood and particulate matter from other types of liquid samples. In other embodiments where it is unnecessary to remove particulate matter from the sample, this component may be omitted. The glucose biosensor 10 generally comprises a sensing electrode 20, a reference electrode 30 and a reagent strip 16. In the version of the sensor depicted in FIGS. 1A–1D, the sensing electrode 20 has a conductive protrusion 18 and reference electrode 30 has a conductive protrusion 19 separated by gap 15. Protrusions 18 and 19 serve as convenient points for electrical connection. Reagent strip 16 is sandwiched between sensing electrode 20 and reference electrode 30 and is in simultaneous contact with the electrically conductive layer 22 of sensing electrode 20 and the electrically conductive layer 32 of reference electrode 30. In the embodiment pictured in FIG. 1D, whole blood separating membrane 38 is interposed between reagent strip 16 and reference electrode 30 in order to filter formed bodies from the blood sample introduced via opening 13. During the time that measurements are taken, electrical contact between sensing electrode 30 and reference electrode 20 is maintained through whole blood separating membrane 38. The sandwich configuration may be optionally held together by clamps, tape and the like. Optionally, spacers 40 may be used to keep sensing electrode 20 and reference electrode 30 physically separated. Spacers 40 may comprise any non-conductive adhesive means, such as adhesives and double sided adhesive tape.

Sensing electrode 20 comprises a non-conductive support member 12 for electrically conductive layer 22. The non-conductive support member may typically be any cohesive non-conductor such as any non-conductive film or sheet forming polymeric material, ceramics, glass, paper, cardboard. The preferred thickness of the non-conductive support material is from about 5 mil to about 10 mil. Polymeric materials, particularly non-conductive polymerics in the form of films or thin sheets are preferred as they may be readily cut to strips of suitable size. In practice non-conductive support 12 is a polymeric film or sheet. Any non-conductive polymeric film or sheet such as polyvinylchloride, polyester, polycarbonate, vinyl acetate copolymer, nylon, poly(1,4-butyleneterephthalate), cellulose propionate, ethylene/acrylic acid copolymer, polybutadiene, polyethylene, polypropylene, polyimide, acrylic film, polyurethane, polystyrene, and polyvinylfluoride may be used. Polyester film such as Mylar® is preferred as it is readily available and easily handled.

Electrically conductive layer 22 of sensing electrode 20 comprises an electrically conductive layer containing a redox mediator. The electrically conductive layer may comprise electrically conductive carbon or graphite, copper, silver, gold, platinum, nickel, stainless steel, iron and other conductive materials and mixtures thereof. Formulations of electrically conductive carbon or graphite containing polymeric materials such as the electrically conductive inks available from Ercon Inc. (Waltham, Mass.) are preferred as they are readily available, can be uniformly spread on a non-conductive support member 12 to form a thin layer and can be easily blended with a redox mediator.

Redox mediators which may be blended with electrically conductive formulations based on electrically conductive inks include dimethylferrocene (DMF), ferricinium, ferrocene monocarboxylic acid (FCOO), 7,7,8,8-tetracyanoquinodimethane (TCNQ), tetrathiafulvalene (TTF), nickelocene (Nc), N-methylacridinium (NMA$^+$), tetrathiatetracene (TTT), N-methylphenazinium (NMP$^+$), hydroquinone or mixtures thereof. DMF is preferred as it gives an easily detectable current change with change of glucose concentration when used in conjunction with a second redox mediator in the reagent strip 16. The preferred concentration of the redox mediator in the electrically conductive layer 22, based on the total weight of the dry electrically conductive layer 22, ranges from about 0.2% to about 15% with concentrations of about 1% to about 9% most preferred. Example 1a illustrates a process for making an embodiment of sensing electrode 20.

Reference electrode 30 comprises a non-conductive support member 12 for electrically conductive layer 32. The non-conductive support member may typically be any cohesive non-conductor such as any non-conductive film or sheet forming polymeric material, ceramics, glass, paper, cardboard. The preferred thickness of the non-conductive support material is from about 5 mil to 10 mil. Polymeric materials, particularly non-electrically conductive polymerics in the form of films or thin sheets are preferred as they may be readily cut to strips of suitable size. In practice, non-conductive support 12 is a polymeric film or sheet. Any non-conductive polymeric film or sheet such as those used for the sensing electrode may be used. Polyester film such as Mylar® is preferred as it is readily available and easily handled.

Electrically conductive layer 32 of reference electrode 30 comprises a Ag/AgCl reference electrode prepared by coating a base support such as polyester film with an electrically conductive formulation comprising Ag/AgCl dispersed in a resin formulation, such as ERCON R-421(DBE-60) Silver/Silver Chloride and curing the coating for about one hour at about 70° C. Other forms of reference electrodes may be used such as the Ag/AgCl reference electrodes described in U.S. Pat. No. 5,401,377, which is herein incorporated by reference to the extent that it is pertinent, and reference electrodes such as standard calomel electrodes may also be used. However, Ag/AgCl electrodes based on Ag/AgCl electrically conductive formulations which may be conveniently spread on a non-conductive base are preferred. Example 1b illustrates a process for making an embodiment of reference electrode 30.

The reagent strip (or carrier strip) 16 comprises a porous matrix, typically a paper, membrane or film, containing an enzyme system and a second redox compound. A porous or fibrous matrix that is a water absorbent strip is preferred for the carrier strip as it can be impregnated with aqueous solutions containing an enzyme system and a redox compound and will readily absorb aqueous samples containing glucose. Any water absorbent porous matrix, in practice a membrane or paper or paper-like material whether cellulosic or a mixture of cellulosic and non-cellulosic components that can be impregnated with the enzyme mixture, the second redox compound, surfactants and stabilizers can be used as a carrier. However, water absorbent porous matrices, typically membranes and papers, that produce a linear correlation of amperometric response to glucose concentration or that produce greater sensitivity and reproducible results with glucose concentration are preferred for the carrier strip. Examples of such water absorbent matrices, membranes and papers are Kimtowel industrial grade paper towel (Kimberly-Clark); Brawny 2-ply paper town (James River Corp., Norwalk, Conn.); Baxter S/P qualitative filter paper Grade 360; Loprosorb or Loprodyne Nylon 66 (Pall Biosupport, East Hills, N.Y.); Biodyne A amphoteric Nylon 66 membrane (Pall); Leukosorb Type A and Type B polyester (Pall).

The water absorbent film or paper comprising the water absorbent carrier (or reagent) strip 16 is impregnated with an enzyme system and a redox compound formulation. The enzyme system and redox compound formulation comprising a second redox mediator generally comprise an aqueous mixture having the following composition: GOX about 100 units/ml to about 2000 units/ml, with about 800 units/ml preferred; HRP about 10 units/ml to about 100 units/ml, with about 80 units/ml preferred.

Compounds and mixtures of compounds that can function as the second redox mediator are compounds that can be oxidized by hydrogen peroxide under catalysis by horseradish peroxidase (HRP) or other similar peroxidases. Such compounds may comprise various substances such as 3,3'5,5'-tetramethylbenzidine (TMB); 3-methyl-2-benzothiazolinone hydrazone hydrochloride and 3-dimethylaminobenzoic acid (MBTH-DMAB); o-dianisidine; o-toluidine; sulfonated 2,4-dichloro-phenol plus 4-amino phenazone; benzidine; 3-methyl-2-benzothiozolinone hydrazone plus 3-(dimethylamino) benzoic acid or 2-methoxy-4-allyl phenol; 4-aminoantipyrene-dimethylaniline and 4-aminoantipyrene-4-methoxynaphthol; salts of ferrocyanide (Fe(CN)$_6^{-4}$); HCN; I$^-$; Co(NH$_3$)$_6^{++}$; Sn$^{+2}$; S$^{--}$; Tl$^{+2}$ and mixtures thereof. Ferrocyanide (Fe(CN)$_6^{-4}$) salts and TMB are preferred as they generally produce relatively large changes in current flow with changes of glucose concentration over a wide range. The enzyme system and redox compound formulation generally contain about 0.1% to about 5% on the weight of the aqueous mixture of the second redox mediator with about 1% preferred.

The formulation used to impregnate reagent strip 16 further comprises about 0.05% to about 8%, with about 0.5% preferred, of a surfactant such as cholic acid, Triton X-100, polyethylene glycol, sodium lauryl sulfate, sodium lauryl sarcosinate, hydroxypropyl methylcellulose ("Methocel" 40-101 personal care grade), tetrapropylene diphenyloxide disulphonate sodium salt ("DOWFAX 2A1"), capryloamphocarboxypropionate ("MIRALOL J2M-SF"), polyoxyethylene-2-cetyl ether, Surfynol 485, MEGA-8, MEGA-10 and mixtures thereof. A preferred surfactant is MEGA 8. More preferred is a mixture of Surfynol 485 and MEGA-8 which improves shelf stability of the sensor.

Another component of the formulation used to impregnate reagent strip 16 is a water soluble or water dispersible aqueous thickening or gelling agent (also known as a stabilizer) which comprises about 0.00005% to about 0.5% of the weight of the formulation, with about 0.0005% preferred. Such thickening or gelling agents may comprise various substances such as gelatin, bovine serum albumin, glutamate, L-arginine, Gantrez, mannitol, gum arabic, polypep (low viscosity), methocel and mixtures thereof used separately or in combination. Gelatin, methocel and mannitol and mixtures thereof are preferred. However, any water soluble or water dispersible aqueous thicknening or gelling agent may be used in the carrier strip providing it does not interfere with the chemical process which occur during glucose assay. Preferred quantities and components generally give a fast, reproducible response.

Yet another component comprising the formulation used to impregnate reagent strip 16 is a buffering agent to maintain the pH between about 4 and about 8. Any buffering agent may be used that can maintain the pH in this range providing it does not interfere with the electron transfer reactions of the biosensor. For example, buffers commonly known in the art such as citrate salts, succinate salts, tris-(hydroxymethyl) aminomethane, phosphate salts, 2(N-morpholino) ethanesulfonic acid and mixtures thereof may be used. Citrate buffer is preferred to maintain the pH in the preferred range of about 4.5 to about 5.5. The preferred concentration of buffer ranges from about 0.00625 mole to about 0.05 mole per sensor reagent strip with the most preferred concentration ranging from about 0.0125 mole to about 0.025 mole.

A version of the sensor of the present invention includes a whole blood treatment component that is used to separate blood plasma from red blood cells. It was obtained either by use of commercially available membranes, such as Prime-Care membrane (Code S) (herein PC), Gelman Cytosep 1660, and Nucleopore membranes or by fabricating membranes or fibrous matrixes. Polymer treated glass fibers, that is, glass fibers of a thickness that increases from those designated as A to those designated as D that are coated with polyvinyl alcohol may be used to create a fibrous matrix. A mixture of A and D fibers herein designated (AVA/DVA), can be used to create a suitable membrane by sintering or other processes known in the art. Membranes can be fabricated from polysulfones, polyamides, celluose derivatives, polyesters, polyvinylalcohol polymers and copolymers or any other film forming polymer or copolymer, alone or in combination, using processes well known in the art such as solution or melt casting. Methods known in the art such as inclusion of leachable materials in the polymer solution or melt can be used to create appropriately sized pores by leaching after membrane formulation. Any membrane having a pore size sufficient to retain red blood cells while allowing the liquid fraction of whole blood to pass through can be used. The PrimeCare (Code S) membrane is preferred.

The embodiments of the present invention may be prepared by processes and procedures disclosed in U.S. patent application Ser. No. 08/471,026, now U.S. Pat. No. 08/5,695,947 which is hereby incorporated by reference. The following examples further illustrate embodiments of the invention:

EXAMPLE 1

This example illustrates preparation of the components of a version of the glucose sensor of the present invention.
A. Preparation of a sensing electrode comprising a mixture of a polymer-based graphite ink with graphite powder and a redox mediator on an inert support:

Equal amounts of graphite ink (e.g. from Ercon Inc. or Acheson Colloids Co.) and graphite powder (e.g. from Fisher Scientific) are mixed. DMF is dissolved in an adequate amount of organic solvent (e.g. toluene/alcohol (1:1), or toluene and/or DBE thinner). The mixture of graphite ink and graphite powder is combined and blended with the DMF in toluene-alcohol to obtain a mixture having a fixed viscosity and a spreadable consistency. The well-mixed graphite/DMF mixture was laid down on a base support (e.g. Mylar or PVC film) and spread with a steel doctor knife with a gap of 6 mil to produce about 2.0 mil evenly distributed dried thin layer. The graphite coating was cured at about 40° C. for ninety minutes.

B. Preparation of a reference electrode from a commercial polymer-based Ag/AgCl ink (e.g. from Ercon Inc.) on an inert support:

The polymeric Ag/AgCl ink was laid down on a base support (e.g. Mylar or PVC film) and spread with a steel doctor knife with a gap of 1 mil to produce an evenly distributed thin layer. The Ag/AgCl coating was cured at 70° C. for one hour. The thickness of dried film was about 0.6 mil.

C. A version of the reagent strip was prepared as follows:

The paper or film comprising the water absorbent reagent strip or carrier is impregnated with an aqueous enzyme system and redox compound formulation having 800 units per ml GOX, 80 units per ml HRP, 1% potassium ferrocyanide, 0.5% Mega 8, 0.0005% gelatin, and about 0.2 M sodium citrate to adjust the pH to 5. Two pieces of approximately 4×8 cm Kimtowel (Kimberly-Clark Corp.) were immersed in this solution for about 20 seconds and then transferred to a nylon net and dried in an oven at 40° C. for 20 minutes. This procedure was repeated once on the previously impregnated paper. The paper was then redried in an oven at 40° C. to constant weight.

D. Preparation of whole blood separation membrane:

A whole blood separation membrane was prepared by immersing a PrimeCare (Code S) polysulfone membrane in a 0.2% MEGA 8 solution for 10 hours and then dried.

E. Alternative methods of preparing the whole blood separation membrane include:

Nucleopore polycarbonate membrane and Whatman glass fiber membranes were modified by coating with polymers such as polyvinylpyrrolidone, polyvinylalcohol, polyacrylic acid, alginic acid, gelatin, ethylcellulose, polyethylene glycol monostearate. Polyvinylpyrrolidone and polyvinylalcohol are preferred for membrane modification. The membranes were immersed in aqueous solutions of the polymers overnight and then dried. Concentrations of the polymer solutions ranged from about 0.1% to about 10% with concentrations of about 0.2% to about 1.0% producing the best separation membranes. The effective pore size of the membranes obtained in this way ranged from about 1 micron to about 10 microns.

The components of A, B, C and D or E were assembled to give one version of the face-to-face sandwich sensor illustrated in FIGS. 1A–1D. In another version, where it is unnecessary to filter particulate matter from the sample, the whole blood separation membrane 38 may be omitted and the face-to-face sandwich may be assembled using only the components of A, B and C.

EXAMPLE 2

Figure 4:
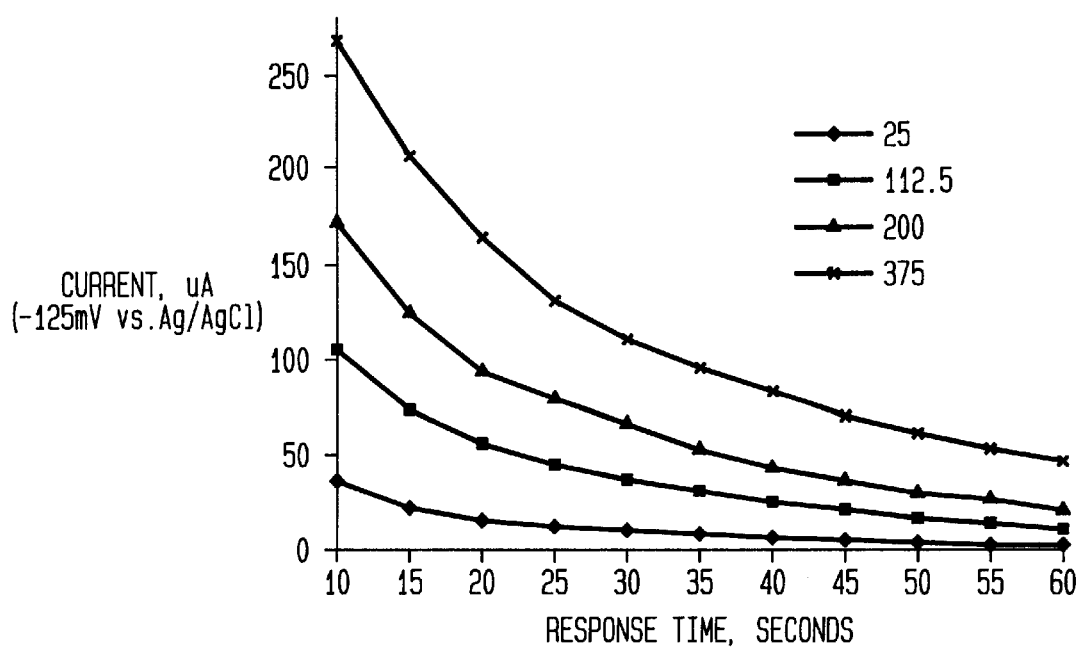
FIG. 4 is a graphical depiction of the kinetics of a version of the glucose sensor that uses the ferrocyanide system.

This example illustrates glucose determination with standard test samples:

Glucose was determined amperometrically with the biosensor of Example 1 under an applied constant potential of 80 to 125 mV supplied by a constant power source. The response at regular intervals was recorded either manually or electronically via a data acquisition system (e.g. by using an IEEE 488 interface in a computer). The timing process was started on the addition of sample (about 25–45 μl) to the biosensor. The current generated from the enzymatic redox reactions was detected by a picoammeter or an electrometer. With appropriate instrumentation, this system allows direct readout of glucose concentration on a meter. The linear range of detection with respect to time was established with four concentrations of commercial glucose serum samples (Verichem Corp.) ranging from 25 to 375 mg/dl. Linear relationships were observed from 15 to 55 seconds. This is shown in FIG. 4.

Figure 5:
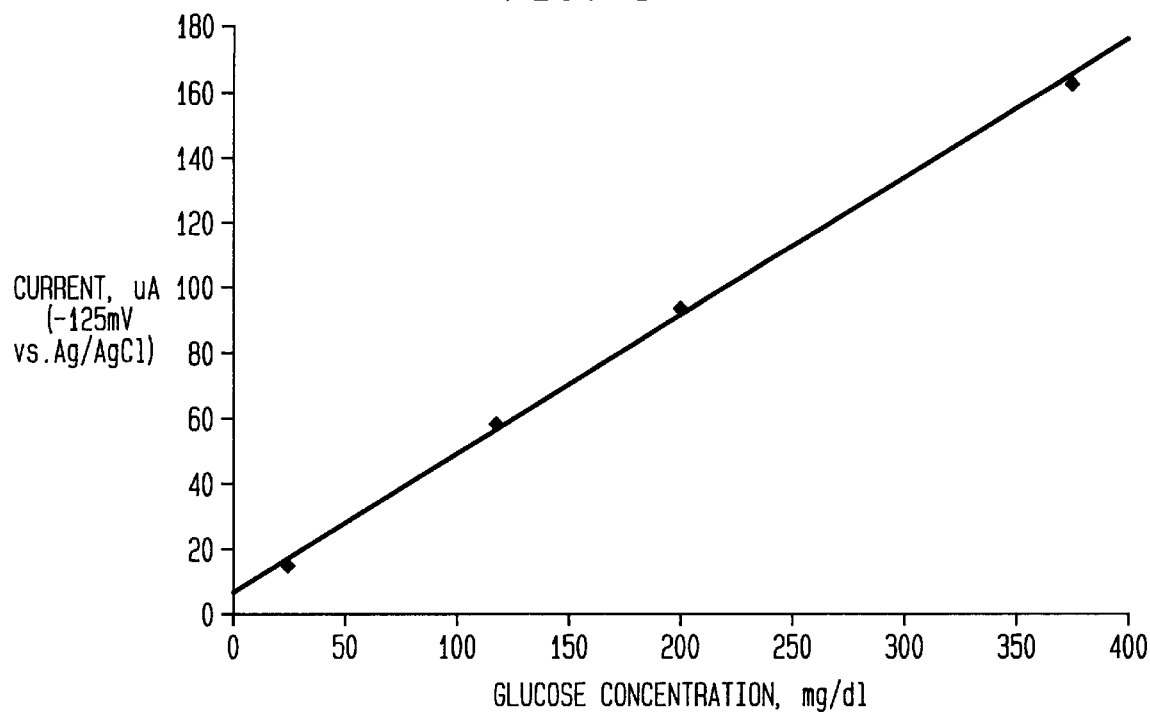
FIG. 5 is a calibration curve of a version of the glucose sensor that uses the ferrocyanide system.

The linear response of the sensor with respect to concentration was determined with concentrations of commercial glucose serum samples (Verichem Corp.) ranging from 25 to 375 mg/dl. This is shown in FIG. 5 which is a calibration curve of glucose concentration vs. current. In this concentration range, linearity of response was achieved in 15 to 55 seconds. The sensitivity of the response curve was about 4.3 μA/10 mg/dl and the intercept of the curve was nearly zero.

EXAMPLE 3

Using the calibration curve established in Example 2, glucose concentrations were determined in samples of fresh human plasma by measuring the current. These results are shown in Table 1. The measured values of glucose concentration using the glucose sensor of Example 1 are virtually identical to the values achieved with the classical AAP-optical method.

TABLE I

Blood Glucose Measurement

| Sample Number | measurement values with AAP - optical method (mg/dl) | measurement values with glucose biosensor* mg/dl (avg.) |
|---|---|---|
| 1 | 82 | 76, 83 (80) |
| 2 | 79 | 81, 77 (79) |
| 3 | 108 | 107, 110 (109) |
| 4 | 100 | 98, 102 (100) |

Obtained from calibration curve established with serum-based glucose reference (Verichem Corp.), levels A–C: 25 mg/dl - 375 mg/dl; first mediator DMF, second mediator TMB, →125 mV constant applied potential.

EXAMPLE 4

This example shows the difference in response of a 2-mediator system vs. a 1-mediator system.

Figure 3:
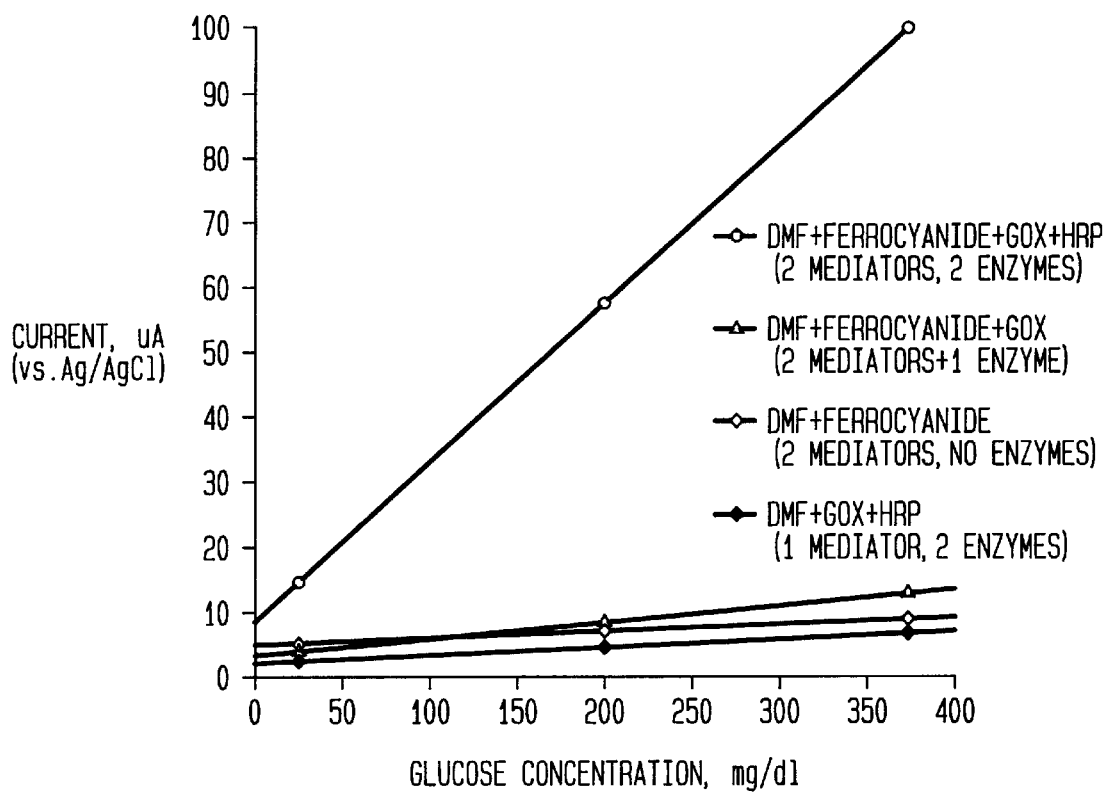
FIG. 3 is a graphical comparison of the response characteristics of various glucose sensors.

A version of the sensor having the sandwich configuration was constructed as in Example 1 using DMF mediator in the sensing electrode and ferrocyanide in the reagent strip. A linear response curve was observed from 25 mg/dl to 375 mg/dl using serum based glucose samples. This is shown in FIG. 3 at line a. On the other hand, a system having only DMF in the sensing electrode as the sole mediator gave practically no response. This is shown in FIG. 3 at line d. The sensitivity was also low for other two cases, no HRP or no GOX and HRP (see FIG. 3, lines b and c).

EXAMPLE 5

This example demonstrates the response of the sensor having the face-to-face sandwich configuration constructed as in Example 1 using DMF mediator in the sensing electrode and TMB in the reaction strip.

Figure 6:
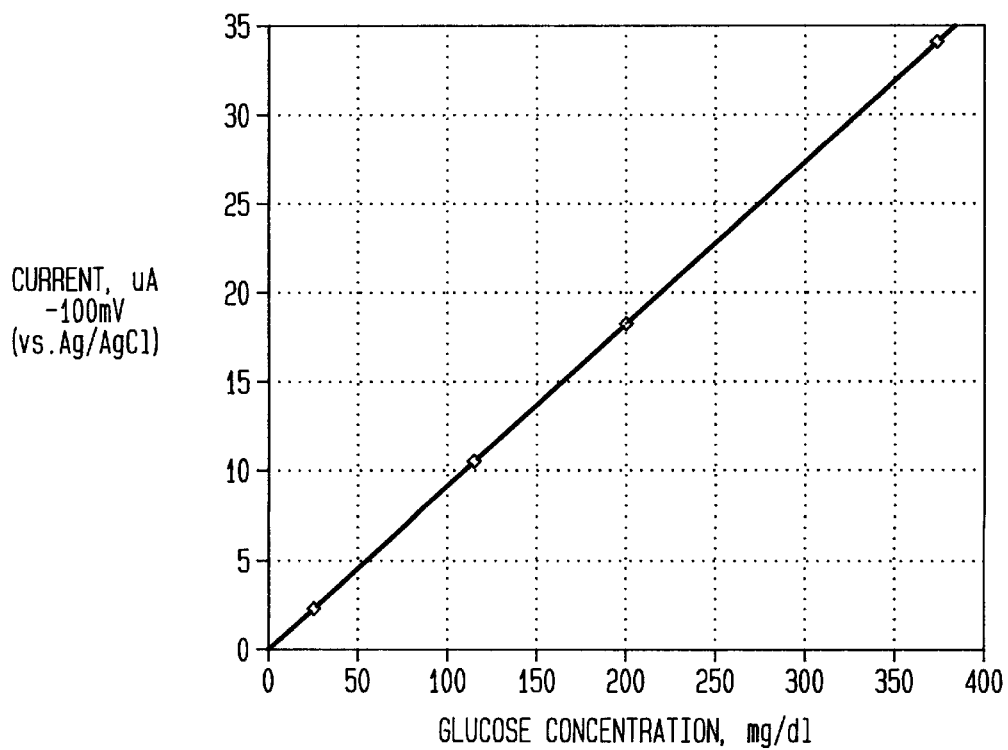
FIG. 6 is a calibration curve of a version of the glucose sensor that uses the TMB system.

The reaction kinetics with TMB in the reagent strip resemble those of the ferrocyanide system of Example 2 as depicted in FIG. 4. FIG. 6 is a calibration curve for this sensor using standard samples having a glucose concentration of 25 mg/dl to 375 mg/dl. The response was highly linear with a sensitivity of about 1 μA/10 mg/dl.

EXAMPLE 6

This example demonstrates how the low cell potential of the version of the amperometric glucose sensor shown in FIGS. 1A–1D completely eliminates or reduces erroneous results produced by oxidizable interfering substances.

Serum samples with l-ascorbic acid concentrations of 0 mg/liter, 4.5 mg/l, 9.0 mg/l, 18 mg/l and 50 and a fixed glucose concentration of 80 mg/dl were assayed for glucose concentration with the biosensor of Example 1 under an applied constant potential of −125 mV supplied by a constant power source. The results shown in Table 2 demonstrate that even at 18 mg/l, an ascorbic acid concentration that exceeds the levels normally found in human serum, there is no effect on the glucose assay. At 50 mg/l ascorbic acid the glucose assay is slightly lower than the known value. Similar results were obtained at potentials of about −80 mV to about −125 mV. At cell potentials of about +100 mV to about +350 mV interference by the ascorbic acid is sufficient to disrupt the quantitative relationship of current flow to glucose concentration.

TABLE 2

Error in Glucose Assay Produced by the Presence L-Ascorbic Acid With Sensor Operating at Low Cell Potential

| l-Ascorbic Acid Concentration mg/l | Glucose Conc. Determined at Cell Potential −125 mV on Serum Having Glucose Conc. 80 mg/dl | Percent Error In Glucose Assay |
|---|---|---|
| 0 | 80 | 0 |
| 4.5 | 80 | 0 |
| 9.0 | 80 | 0 |
| 18 | 80 | 0 |
| 50 | 76 | −5 |

EXAMPLE 7

This example shows that the sensitivity (i.e. the magnitude of current output per unit of glucose concentration) of the sensor can be increased or decreased by adjusting the thickness of the sensing or working electrode.

Figure 7:
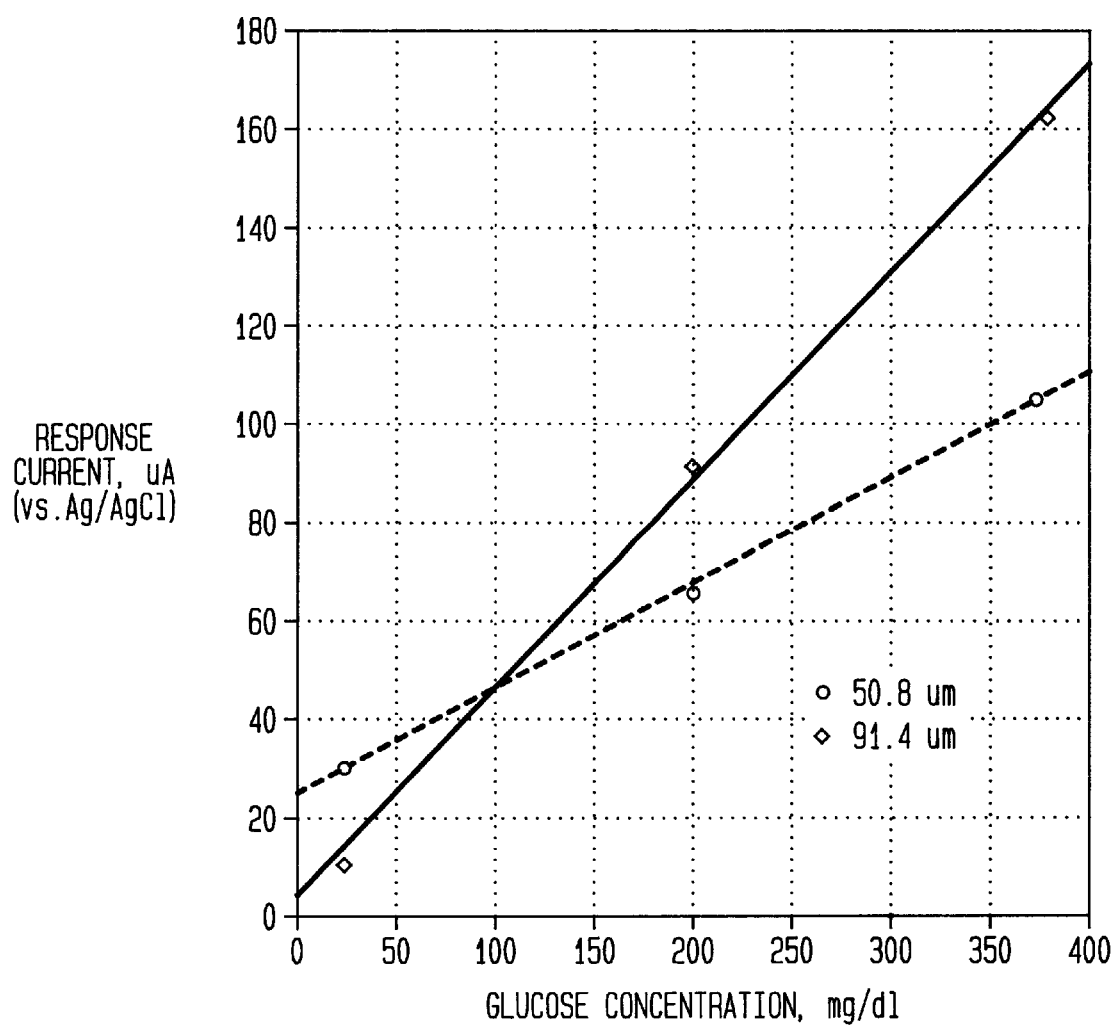
FIG. 7 is a graphical representation of the effect of sensor electrode thickness.

Sensors were constructed as in Example 1, except that the thickness of the conductive layer of the sensing electrode (i.e. the working electrode) was varied. It is seen that an 80% increase in the thickness of the conductive layer increased the sensitivity by 100%. In addition, the increase of thickness greatly reduced the intercept of the glucose calibration curve. Generally, as is known in the art, the lower the intercept the better the precision of the assay. These results are shown in Table 3. FIG. 7 is a graphical representation of these results.

TABLE 3

Effect of Sensing Electrode Conductive Layer Thickness on Sensor Sensitivity

| Conductive Layer Thickness, μm | Percent Increase Thickness | Intercept of Glucose Calibration Curve, μA | Sensitivity μA/10 mg/dl | Percent Increase in Sensitivity |
|---|---|---|---|---|
| 50.8 | — | 23.28 | 2.16 | — |
| 91.4 | 80 | 0.76 | 4.33 | 100 |

EXAMPLE 8

This example demonstrates the shelf stability of different sensor strip formulations.

Two sensors, were constructed as in Example 1. One sensor was provided with a 10 mm×7 mm reagent strip impregnated with formulation A having the following composition: 51.2 IU GOX, 8 IU HRP, 2.4% mannitol, 0.6% sorbitol, 0.0018% gelatin, 0.96% potassium ferrocyanide, 0.072% Surfynol 485, 1.2% Mega 8, and 0.025M citrate buffer pH 5. The second sensor was provided with a 10 mm×7 mm regent strip impregnated with formulation B, which is the same as formulation A except that Surfynol 485 and Mega 8 are absent. According to a standard aging protocol, 1 week at 45° C. is about equivalent to 3 months storage at room temperature, 2 weeks to about 6 months, 3 weeks to about 9 months and 4 weeks to about 1 year. Table 4 summarizes the results of the accelerated aging test. It is seen that the response of the sensor having Surfynol-485 and Mega 8 (formulation A) remained unchanged even after an accelerated test period equivalent to about one year of room temperature storage, while the sensor having formulation B which lacked these components showed significant changes in response during aging.

TABLE 4

Effect of Accelerated Aging on Sensor Response

| Reagent Strip Formulation | Glucose Concentration mg/dl | Current (μA) Produced After Days in Oven at 45° C. | | Percentage Change in Response |
|---|---|---|---|---|
| | | 1 Day | 28 Days | |
| A | 25 | 10 | 10 | 0 |
| A | 375 | 125 | 125 | 0 |
| B | 25 | 10 | 20 | +100 |
| B | 375 | 72 | 58 | −19.4 |

EXAMPLE 9

The example demonstrates the enhanced sensitivity of amperometric sensors arranged in a face-to-face sandwich configuration in which the conductive surfaces of the sensing electrode and the reference electrode face each other with the reagent strip sandwiched between them as pictured in FIGS. 1A–1D, compared to the conventional side-by-side configuration in which the sensing and reference electrodes are arranged parallel to each other with their conductive surfaces facing in the same direction and with the reagent strip forming a bridge between the electrodes. Construction of the amperometric cholesterol sensor is disclosed in U.S. patent application Ser. No. 08/471,026, now U.S. Pat. No. 08/5,695,947 filed Jun. 6, 1995 which is herein incorporated by reference. Construction of the amperometric glycoprotein sensor is disclosed in U.S. patent application Ser. No. 08/914,283, field Aug. 18, 1997 which is herein incorporated by reference.

Table 5 compares the sensitivity of strip sensors constructed in the face-to-face sandwich configuration versus corresponding sensors that have the side-to-side configuration of the electrodes.

TABLE 5

Enhanced Sensitivity of Face-To-Face Sandwich Configuration Amperometric Sensors

| Sensor Type | Sensor Configuration | Sensitivity μA/10 mg/dl | Percentage Increase |
|---|---|---|---|
| Glucose | Face-to-Face Sandwich | 2.16 | 440 |
| | Side-to-Side | 0.4 | — |
| Glycoprotein | Face-to-Face Sandwich | 6.0 (mM/ml) | 46 |
| | Side-to-Side | 4.1 (nM/ml) | — |
| Cholesterol | Face-to-Face Sandwich | 0.39 | 200 |
| | Side-to-Side | 0.13 | — |

It can be seen that in all cases sensitivity of the amperometric sensor is markedly increased by arranging the strip sensor in the face-to-face sandwich configuration. The face-to-face sandwich configuration can enhance the sensitivity of any amperometric method that relies on the transfer of electrons caused by the introduction of an analate.

The advantages of the present invention include the ability to obtain an instantaneous direct measurement of the glucose level of whole blood, serum or plasma without sample treatment or dilution, thus enabling appraisal of the current glycemic state of a patient. Another advantage is the ability to detect and assay glucose on the spot: at home, in a physicians office or in a hospital room. Yet another advantage is the low cost and disposability of the biosensor. A further advantage is the ability of the sensor to function at low and negative applied constant voltage which greatly reduces the potential for interference. Erroneous readings due to interfering substances such as ascorbic acid are virtually eliminated. A still further advantage is the rapid response of the sensor enabling the assessment of a patient's current glycemic state in one minute or less. Yet a further advantage is that the process of determining the current glycemic state of a patient with the sensor of the present invention is simple, convenient and inexpensive making it possible for doctors and nurses or patients and members of the patient's family to perform the assay.

A still further advantage of the method and sensor of the current invention is the ability to use whole blood without separation, making the assay convenient and rapidly performed, thus enabling large numbers of patients to be screened in a short time.

The sensor of the present invention may comprise a kit including electronic means to automatically calculate and or chart a patient's current glycemic state. Although the present invention has been described in considerable detail with reference to certain preferred versions thereof, other versions are possible. For example, other versions of the glucose biosensor are possible as is its use in conjunction with instrumentation such as devices for automatically assaying large numbers of samples. Versions of the glucose biosensor of the present invention may also comprise a portion of an analytical kit. The glucose biosensor of the present invention may also be used to assay a wide variety of glucose containing fluids of biological, agricultural and industrial origin. Therefore, the spirit and scope of the appended claims should not be limited to the description of the preferred versions contained herein.

What is claimed is:

1. An amperometric sensor for the determination of glucose in aqueous media comprising:
   a sensing electrode, the sensing electrode comprising;
      a non-conductive support member, with the non-conductive support member comprising;
         a non-conductive polymeric film;
         the non-conductive polymeric film coated with an electrically conductive layer, with the electrically conductive layer containing;
            a first redox mediator; and
   a reference electrode comprising;
      a non-conductive polymeric film, the polymeric film coated with an electrically conductive formation comprising Ag/AgCl dispersed in a resin formulation, and with the reference electrode having an opening; and
   a reagent strip, the reagent strip comprising;
      a carrier strip that is a porous or fibrous water absorbent matrix, the carrier strip impregnated with a mixture comprising;
         glucose oxidase,
         horseradish peroxidase,
         a second redox mediator that can be oxidized by hydrogen peroxide under catalysis by horseradish peroxidase,
         at least one surfactant,
         at least one stabilizer,
         a buffering agent to maintain a pH from about 4 to about 8;
with the electrically conducting layer of the sensing electrode and the electrically conductive formulation of the reference electrode facing each other; and with the reagent strip superimposed on and in physical contact with the electrically conducting layer of the sensing electrode, and with the reference electrode superimposed on the reagent strip so that the electrically conductive formulation coating the reference electrode is superimposed on the reagent strip and in physical contact with the reagent strip; so that the sensing electrode and the reagent strip and the reference electrode form a sandwich.

2. The sensor of claim 1 in which the non-conductive support member of the sensing electrode comprises a polymeric film strip and the electrically conductive layer of the sensing electrode comprises an electrically conductive carbon or graphite formulation containing the first redox mediator.

3. The sensor of claim 2 in which the reference electrode comprises a Ag/AgCl reference electrode strip comprising a non-conductive polymeric film support member coated with a layer of an electrically electrode formulation comprising Ag and AgCl dispersed in a resin formulation.

4. The sensor of claim 3 in which the first redox mediator contained in the electrically electrode layer of the sensing electrode is selected from the group consisting of dimethylferrocene, ferricinium, ferrocene monocarboxylic acid, 7,7,8,8-tetracyanoquinodimethane, tetrathiafulvalene, nickelocene, N-methylacridinium, tetrathiatetracene, N-methylphenazinium, hydroquinone and mixtures thereof.

5. The sensor of claim 4 in which the second redox mediator contained in the reagent strip is selected from the group consisting of 3,3'5,5'-tetramethylbenzidine, 3-methyl-2-benzothiazolinone hydrazone hydrochloride and 3-dimethylaminobenzoic acid, o-dianisidine, o-toluidine, sulfonated 2,4-dichloro-phenol and 4-amino phenazone benzidine, 3-methyl-2-benzothiozolinone hydrazone and 3-(dimethylamino) benzoic acid, 3-methyl-2-benzothiozolinone hydrazone and 2-methoxy-4-allyl phenol, 4-aminoantipyrene-dimethylaniline and 4-aminoantipyrene-4-methoxynaphthol, $(Fe(CN)_6^{-4})$, HCN, $I^-$, $Co(NH_3)_6^{+2}$, $Sn^{+2}$, $S^{-2}$, $Tl^{+2}$ and mixtures thereof.

6. The sensor of claim 5 in which the surfactant is selected from the group consisting of cholic acid, Triton X-100, polyethylene glycol, sodium lauryl sulfate, sodium lauryl sarcosinate, hydroxypropyl methylcellulose, tetrapropylene diphenyloxide disulphonate sodium salt, capryloamphocarboxypropionate, polyoxyethylene-2-cetyl ether, 2,4,7,9-tetramethyl-5-decyne-4,7-diol ethoxylate, octanoyl-N-methyl-D-glucamide, decanoyl-N-methyl-D-glucamide and mixtures thereof.

7. The sensor of claim 6 in which the stabilizer is selected from the group consisting of gelatin, bovine serum albumin, glutamate, L-arginine, Gantrez, mannitol, gum arabic, low viscosity polypep, methocel and mixtures thereof.

8. The sensor of claim 7 in which the buffer is selected from the group consisting of citrate, succinate, tris-(hydroxymethyl)aminomethane, phosphate, 2(N-morpholino) ethanesulfonic acid and mixtures thereof.

9. The sensor of claim 8 in which the polymeric film comprising the non-constructive support member of the sensing electrode and the non-conductive support member of the reference electrode comprises polyester and the first redox mediator is 1,1'dimethylferrocene and the second redox mediator is selected from the group consisting of 3,3',5,5'tetramethylbenzidine, potassium ferrocyanide and mixtures thereof.

10. The sensor of claim 9 in which the surfactant is selected from the group consisting of 2,4,7,9-tetramethyl-5-decyne-4,7-diol ethoxylate, octanoyl-N-methyl-D-glucamide and mixtures thereof.

11. The sensor of claim 1 further comprising a whole blood separation membrane, the whole blood separation membrane having an effective pore size of about 1 micron to about 10 microns, with the whole blood separation membrane interposed between the reagent strip and the reference electrode and with the whole blood separation membrane superimposed on and in physical contact with the reagent strip and with the reference electrode superimposed on the whole blood separation membrane so that the electrically conductive formulation coating the reference electrode is in physical contact with the whole blood separation membrane; and with the whole blood separation membrane completely covering the opening in the reference electrode.

12. The sensor of claim 11 in which the whole blood separation membrane is selected from the group consisting of PrimeCare (Code S) polysulfone membrane; Gelman Cytosep 1660 membrane; PrimeCare (Code S) polysulfone membrane coated with octanoyl-N-methyl-D-glucamide; polycarbonate membrane having a coating selected from the group consisting of polyvinylpyrrolidone, polyvinylalcohol, polyacrylic acid, alginic acid, gelatin, ethylcellulose, polyethylene glycol monostearate; and glass fiber membranes having a coating selected from the group consisting of polyvinylpyrrolidone, polyvinylalcohol, polyacrylic acid, alginic acid, gelatin, ethylcellulose, polyethylene glycol monostearate.

13. A method for assaying a sample of whole blood for the concentration of glucose contained in the whole blood and fractions thereof, comprising the steps of:

a) providing an amperometric biosensor for glucose comprising;
a sensing electrode, the sensing electrode comprising;
a non-conductive support member, with the non-conductive support member comprising;
a non-conductive polymeric film;
the non-conductive polymeric film coated with an electrically electrode layer, with the electrically conductive layer containing;
a first redox mediator; and
a reference electrode comprising;
a non-conductive polymeric film, the polymeric film coated with an electrically conductive formulation comprising Ag/AgCl dispersed in a resin formulation, and with the reference electrode having an opening; and
a reagent strip, the reagent strip comprising;
a carrier strip that is a porous or fibrous water absorbent matrix, the carrier strip impregnated with a mixture comprising;
glucose oxidase,
horseradish peroxidase,
a second redox mediator that can be oxidized by hydrogen peroxide under catalysis by horseradish peroxidase,
at least one surfactant,
at least one stabilizer,
a buffering agent to maintain a pH from about 4 to about 8; and
a whole blood separation membrane, the whole blood separation membrane comprising a porous matrix;
with the porous matrix having an effective pore size of about 1 micron to about 10 microns;
with the electrically conducting layer of the sensing electrode and the electrically conductive formulation of the reference electrode facing each other; and with the reagent strip superimposed on and in physical contact with the electrically conducting layer of the sensing electrode, and with the whole blood separation membrane superimposed on and in physical contact with the reagent strip; and with the reference electrode superimposed on the whole blood separation membrane; so that the electrically conductive formulation coating the reference electrode is in physical contact with the whole blood separation membrane, and with the whole blood separation membrane completely covering the opening in the reference electrode; so that the sensing electrode and the reagent strip and the whole blood separation membrane and the reference electrode form a sandwich;
b) introducing a whole blood sample into the opening of the reference electrode;
c) maintaining a potential of about −80 mV to about −125 mV across the sensing electrode and the reference electrode;
d) measuring the current passing between the sensing electrode and the reference electrode;
e) comparing the current measured to a calibration curve of the concentration of glucose versus current at the potential used in step c) to obtain the concentration of glucose in the whole blood sample.

14. The method of claim 13 in which the electrically conductive layer of the sensing electrode of step a) comprises an electrically conductive carbon or graphite formulation and the first redox mediator is selected from the group consisting of dimethylferrocene, ferricinium, ferrocene monocarboxylic acid, 7,7,8,8-tetracyanoquinodimethane, tetrathiafulvalene, nickelocene, N-methylacridinium, tetrathiatetracene, N-methylphenazinium, hydroquinone and mixtures thereof.

15. The method of claim 14 in which the second redox mediator contained in the reagent strip of step a) is selected from the group consisting of 3,3'5,5'-tetramethylbenzidine, 3-methyl-2-benzothiazolinone hydrazone hydrochloride and 3-dimethylaminobenzoic acid, o-dianisidine, o-toluidine, sulfonated 2,4-dichloro-phenol and 4-amino phenazone benzidine, 3-methyl-2-benzothiozolinone hydrazone and 3-(dimethylamino) benzoic acid, 3-methyl-2-benzothiozolinone hydrazone and 2-methoxy-4-allyl phenol, 4-aminoantipyrene-dimethylaniline and 4-aminoantipyrene-4-methoxynaphthol, $(Fe(CN)_6^{-4})$, HCN, $I^-$, $Co(NH_3)_6^{+2}$, $Sn^{+2}$, $S^{-2}$, $Tl^{+2}$ and mixtures thereof.

16. The method of claim 15 in which the porous matrix comprising the whole blood separation membrane of step a) is selected from the group consisting of PrimeCare (Code S) polysulfone membrane; Gelman Cytosep 1660 membrane; PrimeCare (Code S) polysulfone membrane coated with octanoyl-N-methyl-D-glucamide; polycarbonate membrane having a coating selected from the group consisting of polyvinylpyrrolidone, polyvinylalcohol, polyacrylic acid, alginic acid, gelatin, ethylcellulose, polyethylene glycol monostearate; and glass fiber membranes having a coating selected from the group consisting of polyvinylpyrrolidone, polyvinylalcohol, polyacrylic acid, alginic acid, gelatin, ethylcellulose, polyethylene glycol monostearate.

17. The method of claim 16 in which the at least one surfactant impregnated in the reagent strip of step a) is selected from the group consisting of cholic acid, Triton X-100, polyethylene glycol, sodium lauryl sulfate, sodium lauryl sarcosinate, hydroxypropyl methylcellulose, tetrapropylene diphenyloxide disulphonate sodium salt, capryloamphocarboxypropionate, polyoxyethylene-2-cetyl ether, 2,4,7,9-tetramethyl-5-decyne-4,7-diol ethoxylate, octanoyl-N-methyl-D-glucamide, decanoyl-N-methyl-D-glucamide and mixtures thereof.

18. The method of claim 17 in which the stabilizer in the reagent strip of step a) is selected from the group consisting of gelatin, bovine serum albumin, glutamate, L-arginine, Gantrez, mannitol, gum arabic, low viscosity polypep, methocel and mixtures thereof.

19. The method of claim 18 in which the buffering agent in the reagent strip of step a) is selected from the group consisting of citrate, succinate, tris-(hydroxymethyl) aminomethane, phosphate, 2(N-morpholino) ethanesulfonic acid and mixtures thereof.

20. A method of enhancing the sensitivity of an amperometric strip sensor for the assay of an analyte comprising the steps of:
a) forming a sensing electrode, the sensing electrode comprising;
a non-conductive support member, with the non-conductive support member comprising;
a non-conductive polymeric film;
the non-conductive polymeric film coated with an electrically conductive layer, with the electrically conductive layer containing;
a first redox mediator; and
b) forming a reference electrode comprising;
a non-conductive polymeric film, the polymeric film coated with an electrically conductive formulation comprising Ag/AgCl dispersed in a resin formulation,
c) providing an opening in either electrode for introduction of a sample; and d) forming a reagent strip, the reagent strip comprising;
   a carrier strip that is a porous or fibrous water absorbent matrix, the carrier strip impregnated with a mixture comprising;
   reagents that produce a flow of electrons when contacted by the analyte,
   at least one surfactant,
   at least one stabilizer,
e) arranging the sensing electrode and the reference electrode and the reagent strip so that the electrically conductive layer of the sensing electrode and the electrically conductive formulation of the reference electrode face each other with the reagent strip superimposed on and in physical contact with the electrically conducting layer of the sensing electrode, and with the reference electrode superimposed on the reagent strip so that the electrically conductive formulation coating the reference electrode is in physical contact with the reagent strip; so that the sensing electrode and the reagent strip and the reference electrode form a sandwich.

21. The method of claim 20 further comprising formation of a filtration or treatment layer and interposing the filtration or treatment layer between the reagent strip and the opening in either electrode so that he filtration or treatment layer covers the opening.

22. The method of claim 21 in which the filtration or treatment layer completely covers the reagent strip so that the reagent strip does not make physical contact with the electrode having the opening.

* * * * *